United States Patent
Meconi et al.

(10) Patent No.: US 6,274,165 B1
(45) Date of Patent: Aug. 14, 2001

(54) TRANSDERMAL, HORMONE-DELIVERING THERAPEUTIC SYSTEM

(75) Inventors: Reinhold Meconi, Neuwied; Frank Seibertz, Bad Hönningen, both of (DE)

(73) Assignee: LTS Lohmann Therapie-Systeme AG (DE)

( * ) Notice: Subject to any disclaimer, the term of this patent is extended or adjusted under 35 U.S.C. 154(b) by 0 days.

(21) Appl. No.: 09/341,212

(22) PCT Filed: Jan. 3, 1998

(86) PCT No.: PCT/EP98/00014

§ 371 Date: Aug. 25, 1999

§ 102(e) Date: Aug. 25, 1999

(87) PCT Pub. No.: WO98/31349

PCT Pub. Date: Jul. 23, 1998

(51) Int. Cl.⁷ .............................. A61F 13/02; A61F 13/00
(52) U.S. Cl. ........................ 424/448; 424/449; 424/443
(58) Field of Search ................................. 424/449, 448, 424/447

(56) References Cited

U.S. PATENT DOCUMENTS

| | | | |
|---|---|---|---|
| 4,379,454 | * 4/1983 | Campbell et al. | 604/897 |
| 4,906,169 | * 3/1990 | Chien et al. | 424/448 |
| 5,306,503 | * 4/1994 | Muller et al. | 424/449 |
| 5,393,529 | * 2/1995 | Hoffmann et al. | 424/445 |
| 5,891,920 | * 4/1999 | Hirano et al. | 514/625 |

FOREIGN PATENT DOCUMENTS

| | | |
|---|---|---|
| 32 95 258 A1 | 2/1982 | (DE) . |
| 39 33 460 A1 | 10/1989 | (DE) . |
| 40 20 144 A1 | 6/1990 | (DE) . |
| 0 275 716 B1 | 12/1987 | (EP) . |

* cited by examiner

Primary Examiner—Thurman K. Page
Assistant Examiner—Isis Ghali
(74) Attorney, Agent, or Firm—D. Peter Hochberg; Katherine R. Vieyra; William H. Holt

(57) ABSTRACT

An active compound-containing patch for the controlled delivery of oestradiol or its pharmaceutically acceptable derivatives, alone or in combination with gestagens, to human or animal skin, having an active compound-containing reservoir based on ethylcellulose and contact adhesives comprising adhesive resins is characterized by a contact adhesive having a high plasticizer content.

17 Claims, No Drawings

TRANSDERMAL, HORMONE-DELIVERING THERAPEUTIC SYSTEM

The invention relates to an active compound-containing patch for the controlled delivery of oestradiol or its pharmaceutically acceptable derivatives, alone or in combination with gestagens, to human or animal skin, having an active compound-containing reservoir based on ethylcellulose and contact adhesives comprising adhesive resins.

Transdermal therapeutic systems have been known for a relatively long time, in particular also for the transdermal administration of hormones, especially oestrogens, if appropriate in combination with gestagens.

The active compounds are provided for this in an active compound reservoir based on contact adhesives, whose adhesiveness must guarantee adequate skin contact on application without excessive softening and without skin irritation occurring, and whose absorption and release of active compound must conform to the desired continuous systemic supply of active compound through the skin.

As a basis for reservoir layers comprising oestradiol, inter alia, different materials based on rubber or polyacrylate, in particular comprising ethanol, have already been proposed (e.g. DE-A-32 05 258 and EP-0 275 716).

DE-A-39 33 460 describes active compound patches based on homo- and copolymers comprising at least one derivative of acrylic or methacrylic acid, which are additionally intended to contain water-swellable substances.

DE-B 40 20 144 discloses a transdermal system, optionally also containing hormone, comprising at least one self-adhesive active compound layer, which besides polyacrylate and a film-forming agent compatible therewith should contain a wide quantitative range of plasticizing active compounds and auxiliaries.

A recently described transdermal therapeutic system (see DE-A 195 00 662) comprises an active compound reservoir, containing an oestradiol and, if appropriate, gestagens, based on ethylcellulose having a high proportion of esters of optionally hydrogenated colophony as a tackifying resin together with up to 20% by weight of lauric acid, which is intended to counteract recrystallization of the active compound and thus a decrease in its release rate.

Surprisingly, it has now been found that an unexpectedly high active compound release of oestradiol and in particular norethindrone acetate can be achieved from an active compound reservoir based on ethylcellulose and tackifying resin which is provided with an unusually high proportion of plasticizer.

The patch according to the invention of the type mentioned at the outset is accordingly characterized in that the contact adhesive contains a high proportion of plasticizer.

In particular, the contact adhesive contains at least 15% by weight, preferably at least 20% by weight, of plasticizer.

The active compound-containing patch can otherwise contain emulsifiers, antioxidants and absorption enhancers.

Such a patch can be employed, in particular, for a high combined release of both oestradiol and norethindrone acetate.

Preferred formulations of such hormone-containing contact adhesive materials according to the invention have the following composition (in % by weight):

| | |
|---|---|
| Ethylcellulose | 5–25% |
| Tackifying resins | 10–70% |
| Plasticizer/emulsifiers | 20–40% |
| Oestradiol | 1–10% |
| Norethindrone acetate and/or other gestagens | 1–15% |

Although the addition of plasticizers to active compound-containing contact adhesive materials is known per se, such as, for example, also according to the said DE-A 40 20 144, addition of plasticizer to the customary contact adhesives based on polyacrylates, block copolymers and polyisobutylenes is only possible to a limited extent, since from a certain concentration the cohesion of the contact adhesives decreases and they thus become unsuitable for transdermal application.

The fact that just materials based on ethylcellulose/adhesive resin with unusually high additions of plasticizer would afford particularly useful transdermal therapeutic systems with increased skin penetration of the hormones and a particularly low recrystallization tendency thereof together with good wearing properties of the TTS was in no way to be foreseen, as the said, only recently disclosed TTS development having an active compound reservoir based on ethylcellulose/adhesive resin shows, which as an additive contains lauric acid and not—as now—high proportions of plasticizer.

The composition according to the invention of the active compound reservoir based on ethylcellulose/adhesive resin with a high proportion of plasticizer, but without lauric acid, shows a markedly increased release of hormone compared with the materials according to DE-A 195 00 662, in particular on incorporation of a combination of oestradiol and norethindrone acetate.

This is illustrated by the results given below (Tables 1 and 2), of which Table 1 shows the composition of the investigated materials and Table 2 the results of series of tests on the release of active compound.

It is to be seen that by means of the plasticizer content according to the invention a clear improvement in the release and penetration of active compound is achieved.

TABLE 1

| | Formulations Composition in % | | | | | | |
|---|---|---|---|---|---|---|---|
| Constituents/examples | 1 | 2 | 3 | 4 | 5 | 6 | 7 |
| Ethylcellulose | 15.7 | 14.0 | 14.0 | 14.0 | 14.0 | 14.0 | 14.0 |
| Staybelite Ester 5E | 57.3 | 51.1 | 51.1 | 51.1 | 51.1 | 51.1 | 51.1 |
| Oestradiol | 2.0 | 2.0 | 2.0 | 2.0 | 2.0 | 2.0 | 2.0 |
| NeA | 5.0 | 5.0 | 5.0 | 5.0 | 5.0 | 5.0 | 5.0 |
| IPM | 20.0 | — | — | — | — | — | — |
| Renex 698 | — | 27.9 | — | — | — | — | — |
| Brij 92 | — | — | 27.9 | — | — | — | — |
| Brij 30 | — | — | — | 27.9 | — | — | — |
| Miglyol 812 | — | — | — | — | 27.9 | — | — |
| Lemon oil | — | — | — | — | — | 27.9 | — |
| Eutanol G | — | — | — | — | — | — | 27.9 |

The meanings here are:

| | |
|---|---|
| Staybelite Ester 5E | Glycerol ester of partially hydrogenated colophony |
| NeA | Norethindrone acetate |
| IPM | Isopropyl myristate |
| Renex 698 | Polyoxyethylene-(9)-nonylphenol |
| Brij 92 | Polyoxyethylene-(2)-oleyl alcohol |
| Brij 30 | Polyoxyethylene-(4)-lauryl alcohol |
| Miglyol 812 | Medium chain triglycerides |
| Eutanol G | 2-Octyldodecanol |

TABLE 2

Release of active compound

| Examples | Area weight g/m² | Content mg/16 cm² (n = 3) | | in vitro release μg/16 cm² (n = 3) | | | | | | Guinea-pig skin penetration μg/16 cm² 24–28 h (n = 3) | |
|---|---|---|---|---|---|---|---|---|---|---|---|
| | | | | Oes | | | NeA | | | | |
| | | Oes | NeA | 1 | 2 | 3 | 1 | 2 | 3 | Oes | NeA |
| 1 | 92.3 | 3.0 | 7.5 | 339 | 537 | 684 | 388 | 681 | 1000 | 171 | 75 |
| 2 | 97.8 | 3.2 | 7.2 | 527 | 717 | 763 | 602 | 825 | 866 | 73 | 31 |
| 3 | 95.1 | 3.2 | 7.0 | 291 | 508 | 705 | 391 | 716 | 1029 | 175 | 98 |
| 4 | 109.7 | 3.7 | 8.7 | 267 | 432 | 551 | 396 | 604 | 906 | 221 | 144 |
| 5 | 79.6 | 2.6 | 6.2 | 372 | 558 | 723 | 395 | 687 | 977 | 138 | 58 |
| 6 | 109.1 | 3.9 | 9.5 | 339 | 503 | 647 | 372 | 633 | 960 | 166 | 53 |
| 7 | 96.0 | 3.3 | 7.9 | 306 | 488 | 635 | 392 | 680 | 999 | 138 | 63 |

What is claimed is:

1. Active compound-containing patch for the controlled delivery of oestradiol or its pharmaceutically acceptable derivatives alone or in combination with gestagen to human or animal skin consisting essentially of an active compound-containing reservoir based on ethylcellulose and contact adhesives wherein the contact adhesive has a proportion of plasticizer of at least 15% by weight.

2. The patch of claim 1 wherein the contact adhesive comprises adhesive resins specifically excluding n-substituted o-toluidines.

3. The patch of claim 2 further comprising esters of optionally hydrogenated colophony as a tackifying resin.

4. The patch of claim 2 further comprising an emulsifier content in the contact adhesive of at least 15% by weight.

5. An active compound-containing patch for the controlled delivery of oestradiol or its pharmaceutically acceptable derivatives alone or in combination to human or animal skin comprising:
   5–25% by weight of ethylcellulose
   10–70% by weight of tackifying resin
   20–40% by weight of plasticizer and emulsifiers
   1–10% by weight of oestradiol content
   1–15% by weight of gestagen.

6. The patch of claim 5 wherein the gestagen comprises norethindrone acetate.

7. The patch of claim 2 further comprising a content of antioxidants and adsorption enhancers in the contact adhesive.

8. The patch of claim 2 further comprising a content of absorption enhancers.

9. The patch of claim 2 further comprising a content of antioxidants.

10. Active compound-containing patch for the controlled delivery of estradiol or its pharmaceutically acceptable derivatives alone or in combination with gestagen to human or animal skin consisting of:
   (a) an active compound-containing reservoir based on ethyl cellulose;
   (b) contact adhesive wherein the contact adhesive has a proportion of plasticizer of at least 15% by weight;
   (c) esters of optionally hydrogenated colophony as a tackifying resin;
   (d) a content of absorption enhancers; and
   (e) a content of antioxidants.

11. The active compound-containing pouch according to claim 10 wherein said plasticizer is isopropyl myristate.

12. The active compound-containing pouch according to claim 10 wherein said plasticizer is polyoxyethylene-(9) nonylphenol.

13. The active compound-containing pouch according to claim 10 wherein said plasticizer is polyoxyethylene-(2)-oleyl alcohol.

14. The active compound containing pouch according to claim 10 wherein said plasticizer is polyoxyethylene-(4)-lauryl alcohol.

15. The active compound containing pouch according to claim 10 wherein said plasticizer is medium chain triglycerides.

16. The active compound-containing pouch according to claim 10 wherein said plasticizer is 2-Octyldodecanol.

17. The active compound patch for the controlled delivery of estradiol or its pharmaceutically acceptable derivatives alone or in combination with gestagen to human or animal skin consisting essentially of:
   (a) an active compound-containing reservoir based on ethyl cellulose;
   (b) contact adhesives wherein the contact adhesive has a proportion of plasticizer of at least 15% by weight and an emulsifier content of at least 15% by weight,
   (c) esters of optionally hydrogenated colophony as a tackifying resin;
   (d) a content of absorption enhancers; and
   (e) a content of antioxidants and specifically excluding N-substituted o-toluidines.

* * * * *